US012708401B1

(12) United States Patent
Alsaif et al.

(10) Patent No.: US 12,708,401 B1
(45) Date of Patent: Aug. 18, 2026

(54) SURGICAL INSTRUMENT AND METHOD OF USING THE SAME

(71) Applicant: KING SAUD UNIVERSITY, Riyadh (SA)

(72) Inventors: Rand Fahad Alsaif, Riyadh (SA); Rayan Bakur Alkurdi, Riyadh (SA); Reham Nasser Al Jasser, Riyadh (SA); Saleh Sami Aloraini, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/556,371

(22) Filed: Mar. 4, 2026

(51) Int. Cl.
*A61B 17/322* (2006.01)
*A61B 17/00* (2006.01)

(52) U.S. Cl.
CPC .. *A61B 17/322* (2013.01); *A61B 2017/00477* (2013.01)

(58) Field of Classification Search
CPC .................. A61B 17/322; A61B 17/32; A61B 2017/00477
See application file for complete search history.

(56) References Cited

U.S. PATENT DOCUMENTS 86,741 A * 2/1869 Dutton .................... A47J 17/02 30/280
117,839 A * 8/1871 Watt's ...................... A43D 5/10 30/283
2,426,381 A * 8/1947 Vermillion ........... A61B 17/322 606/132
2,579,029 A * 12/1951 Barker ................. A61B 17/322 D24/146
3,688,407 A * 9/1972 Paquette et al. ... A61B 17/3211 30/301
4,665,915 A * 5/1987 Grollimund ........... A61B 17/32 606/132

(Continued)

FOREIGN PATENT DOCUMENTS

EP 4275627 A1 11/2023
WO 2025064686 A1 3/2025

OTHER PUBLICATIONS

Skill Ayurveda Praveen Patil, "Humby's Skin Grafting Knife | Plastic Surgery Instrument", YouTube Video, First available online Oct. 13, 2021.

(Continued)

*Primary Examiner* — Ryan J. Severson
(74) *Attorney, Agent, or Firm* — Nath, Goldberg & Meyer; Joshua B. Goldberg

(57) ABSTRACT

A surgical instrument includes a handle, a coupling mechanism connected to the handle and a cutting tool. The coupling mechanism includes a body, a first shank movably connected to the body and selectively affixable to the body, and a second shank movably connected to the body and selectively affixable to the body. The first and second shanks may extend from opposite side surfaces of the body. The cutting tool is selectively connectable to the first and second shanks. A method of using the surgical instrument includes selectively connecting the cutting tool to the coupling mechanism. The method includes grasping the handle, directing the cutting tool toward a body portion of a patient, and pressing the cutting tool into a soft tissue of the patient such that the cutting tool can cut into the soft tissue.

20 Claims, 7 Drawing Sheets

(56) References Cited

U.S. PATENT DOCUMENTS 4,690,139 A * 9/1987 Rosenberg ........... A61B 17/322 606/132
5,156,607 A * 10/1992 Kansas ............... A61F 9/00736 606/107
5,330,495 A * 7/1994 Dettwiler ............. A61B 17/322 606/167
5,601,584 A * 2/1997 Obagi .................. A61B 17/322 606/172
5,830,225 A * 11/1998 Detsch ............. A61B 17/32093 606/183
6,755,837 B2 * 6/2004 Ebner ................ A61B 17/1659 600/570
6,840,941 B2 * 1/2005 Rogers ............... A61B 17/1604 606/84
7,645,291 B2 * 1/2010 Ross ....................... A61F 9/013 606/166
7,674,265 B2 * 3/2010 Smith ................ A61B 17/1671 606/79
7,708,746 B2 * 5/2010 Eriksson ................. A61L 27/60 606/132
8,277,217 B2 * 10/2012 Park ......................... A61C 3/02 433/144
8,529,568 B2 * 9/2013 Bouadi .......... A61B 17/320016 606/84
9,226,764 B2 * 1/2016 O'Neil ........... A61B 17/320016
9,610,093 B2 * 4/2017 Sabir ...................... A61B 18/08
9,987,473 B2 * 6/2018 Knowlton ........ A61B 17/32093
10,123,819 B2 * 11/2018 Mahaffey ............... A61B 17/32
10,537,355 B2 * 1/2020 Sabir .................... A61B 17/322
10,773,064 B2 * 9/2020 Knowlton ........... A61M 35/003
11,090,473 B2 * 8/2021 Knowlton ............ A61B 17/322
2004/0225309 A1 11/2004 Eriksson et al.
2006/0064102 A1 * 3/2006 Ebner ................ A61B 17/1659 606/84
2006/0111722 A1 * 5/2006 Bouadi .............. A61B 17/1604 606/79
2006/0271070 A1 * 11/2006 Eriksson .............. A61B 17/322 606/131
2008/0077150 A1 * 3/2008 Nguyen ............. A61B 17/1671 606/85
2008/0077241 A1 * 3/2008 Nguyen ................ A61F 2/4684 606/85
2010/0234849 A1 * 9/2010 Bouadi .......... A61B 17/320708 606/84
2011/0136075 A1 6/2011 Park et al.
2013/0204273 A1 * 8/2013 Sabir .................... A61B 17/322 606/132
2013/0238006 A1 * 9/2013 O'Neil ................... A61B 17/32 606/170
2017/0172599 A1 * 6/2017 Sabir ...................... A61B 18/08
2022/0039780 A1 2/2022 Kern

OTHER PUBLICATIONS

Skill Ayurveda Praveen Patil, "Humby's Knife—Dr Praveen Patil", YouTube Video, First available online Dec. 9, 2021.

Bone Doctor, "How Thick is a Skin Graft!? ", YouTube Video, First available online Jun. 20, 2023.

Bembde Plastic Cosmetic Burns Hand Surgery, "Skin graft harvesting using advanced dermatome for uniform thin graft for faster scarless healing", YouTube Video, First available online Aug. 7, 2022.

* cited by examiner

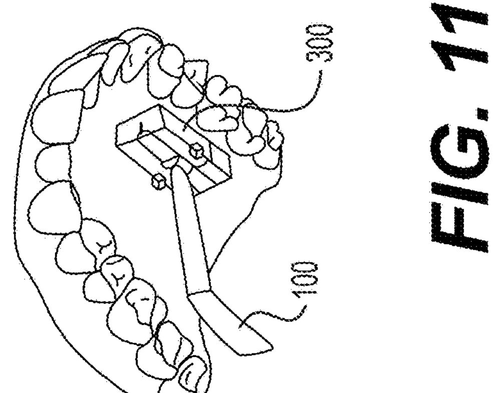
FIG. 11
410
FIG. 13
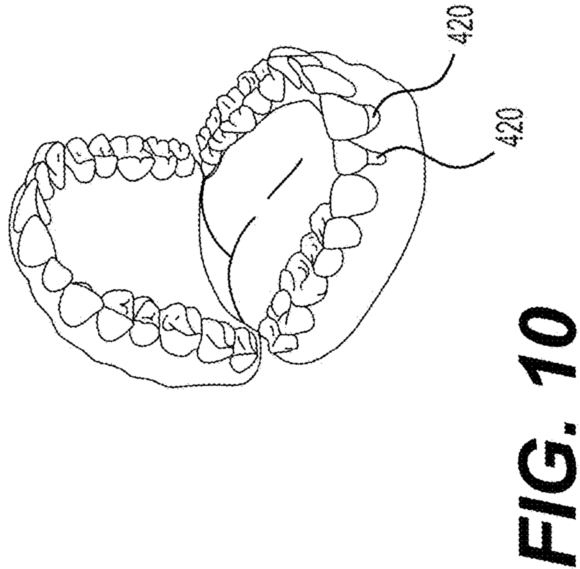
FIG. 10
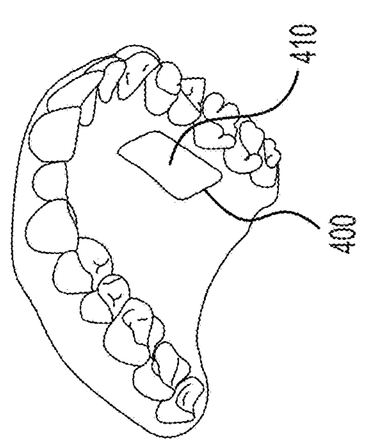
FIG. 12

SURGICAL INSTRUMENT AND METHOD OF USING THE SAME

BACKGROUND

Field

The disclosure of the present patent application relates to surgical procedures, and more particularly, to a surgical instrument and a method of using the same to cut into the soft tissue of a patient.

Description of Related Art

Some surgical procedures require removing an area of soft tissue from a donor body part of a patient and grafting the removed tissue to another body part. The process of removing soft tissue from a donor area carries certain risks, such causing significant postoperative pain and lengthening the recovery period when the harvested graft is too thick (from harvesting too deep into the donor soft tissue), risking the graft to fail from being too thin (when harvesting from a shallow depth), etc. Thus, a surgical instrument and a method of using the same solving the aforementioned problems are desired.

SUMMARY

The present subject matter relates to a handheld surgical instrument and a method of using the instrument for facilitating the process of harvesting a soft tissue graft of a desired shape, size and thickness from a donor site of a patient, for example. The instrument has a handle, a cutting tool and a coupling mechanism for connecting the cutting tool with the handle. The cutting tool may have an elongated hollow polygonal shape. Each sidewall of the polygon may be a cutting blade. More specifically, the edges at the end of the polygon that is distal to the handle may be sharpened.

The instrument of the present subject matter works by grasping the handle and pushing (or pressing) the sharp end of the polygonal cutting tool against a donor soft tissue site of a patient. Due to the pressure exerted on the soft tissue, the sharp edges of the polygonal cutting tool penetrate the soft tissue (e.g., enter the soft tissue in its depth direction). Stated otherwise, an instrument of the present subject matter can be used to make a push cut into soft tissue, cutting the soft tissue in accordance with the shape and the size of the polygonal cutting tool.

The sharp edges of the polygonal cutting tool may be coplanar with one another. Therefore, a push cut made with an instrument of the present subject matter can have a substantially equal depth along the polygonal perimeter of the cut. Depth markings (e.g., in millimeters) may be added to one or more of the sidewalls/cutting blades of the polygonal cutting tool to indicate to a surgeon the depth of entry into soft tissue. The polygonal cutting tool may have a fixed/preset shape or may have an adjustable shape, where two or more sidewalls/cutting blades of the polygon can be selectively elongated or retracted to increase or decrease the size (e.g., boundary) of the cut. Therefore, an apparatus in accordance with the present teachings can be used to cut the boundary of a soft tissue graft and to set the depth of the soft tissue graft via the same push cut.

Having set the perimeter and depth of the graft in a donor soft tissue area by using an instrument according to the present subject matter, a medical professional can then remove (e.g., peel) the soft tissue graft from the donor area by using various other medical instruments and/or applicable techniques. The apparatus of the present subject matter can be used to facilitate the removal of a graft from the soft palate, which can then be grafted to a different region of the mouth, the removal of skin from a donor site, which can be grafted to another body part, etc.

The surgical instrument includes a handle and a coupling mechanism connected to the handle. The coupling mechanism includes a body, a first shank movably connected to the body and selectively affixable to the body, and a second shank movably connected to the body and selectively affixable to the body. The first and second shanks extend from opposite side surfaces of the body. The surgical instrument further includes a cutting tool selectively connectable to the first and second shanks.

These and other features of the present subject matter will become readily apparent upon further review of the following specification.

BRIEF DESCRIPTION OF THE DRAWINGS

The above and other features of the present disclosure will become more apparent by describing in detail exemplary embodiments thereof in conjunction with the accompanying drawings, in which:

FIG. 10 is a first perspective view, illustrating a mouth of a patient that needs oral surgery.

FIG. 11 is a second perspective view, illustrating the surgical instrument of FIG. 1 being pressed into the soft palate of the patient's jaw according to a method step of the present subject matter.

FIG. 12 is a third perspective view, illustrating a perimeter of a cut made into the soft palate using the surgical instrument of FIG. 1.

FIG. 13 is a fourth perspective view, illustrating the soft palate graft removed from the perimeter of cut delineated in FIG. 12 and grafted into the lower jaw to cover exposed roots of teeth, according to a method step of the present subject matter.

Similar reference characters denote corresponding features consistently throughout the attached drawings.

DETAILED DESCRIPTION

Figure 1:
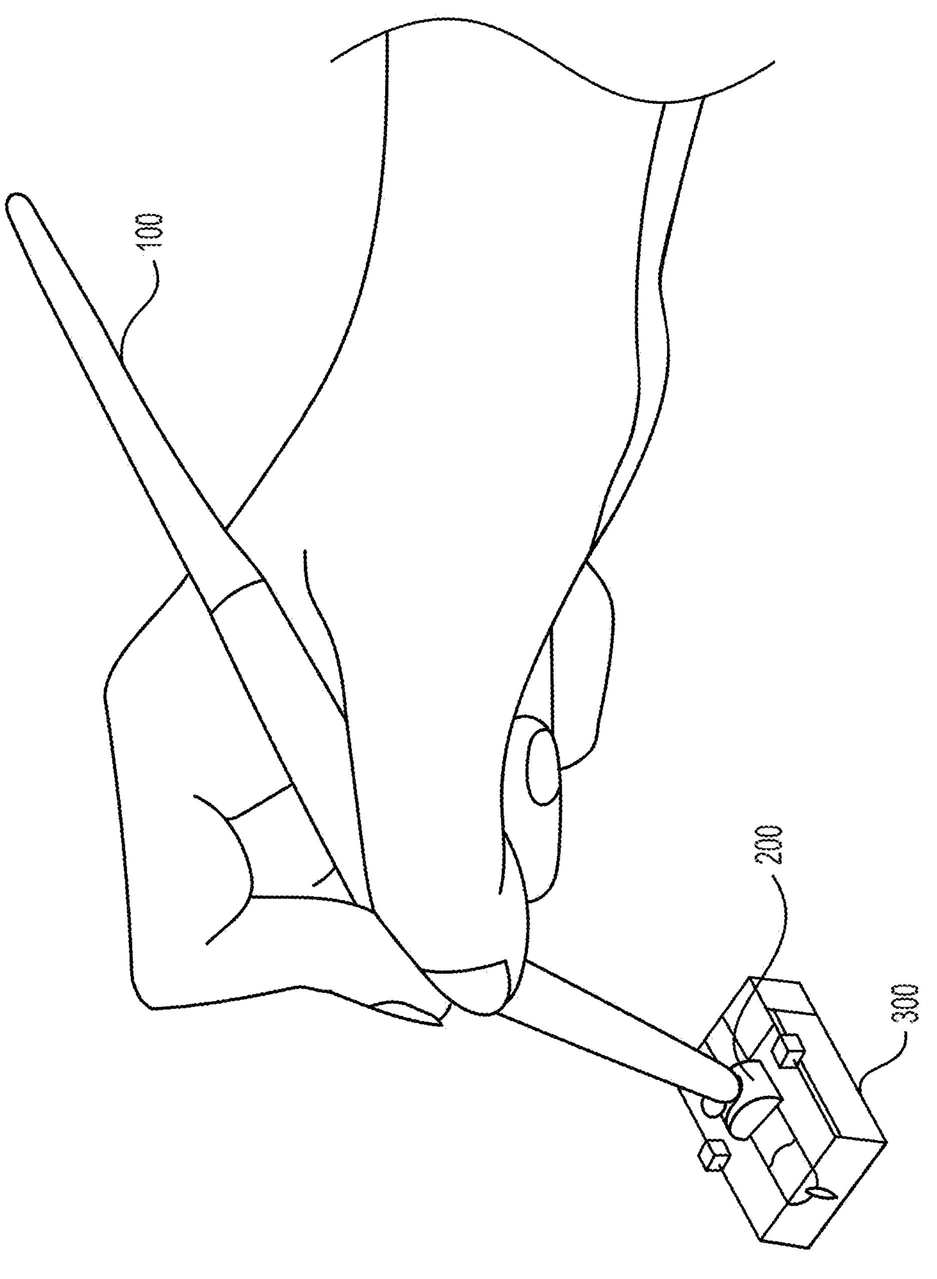
FIG. 1 is a perspective view illustrating a surgical instrument according to an embodiment of the present subject matter, usable in a surgical procedure.
Figure 1:

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms “a”, “an”, and “the” may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms “include,” “includes”, “including,” “have,” “has,” or “having” should be generally understood as open-ended and non-limiting unless specifically stated otherwise.

The use of the singular herein includes the plural (and vice versa) unless specifically stated otherwise. In addition, where the use of the term “about” is before a quantitative value, the present teachings also include the specific quantitative value itself, unless specifically stated otherwise. As used herein, the term “about” refers to a ±10% variation from the nominal value unless otherwise indicated or inferred.

The term “optional” or “optionally” means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

FIGS. 1-8 illustrate a surgical instrument according to an embodiment of the present subject matter. The surgical instrument of FIGS. 1-8 can be used in a surgical procedure to facilitate the process of obtaining a soft tissue graft of a desired shape, size and thickness from a donor area of a patient’s body. The obtained soft tissue graft can, merely as an example, be grafted onto a different body portion of the patient.

Referring to FIGS. 1-8, the surgical instrument includes a handle 100, a coupling mechanism 200 connected to the handle 100, and a cutting tool 300. The handle 100 and the coupling mechanism 200 may be made of a metal, a plastic material, wood, or a combination of these materials, as non-limiting examples. The cutting tool 300 may be made of a metal, for example, steel (e.g., surgical grade stainless steel).

Figure 2:
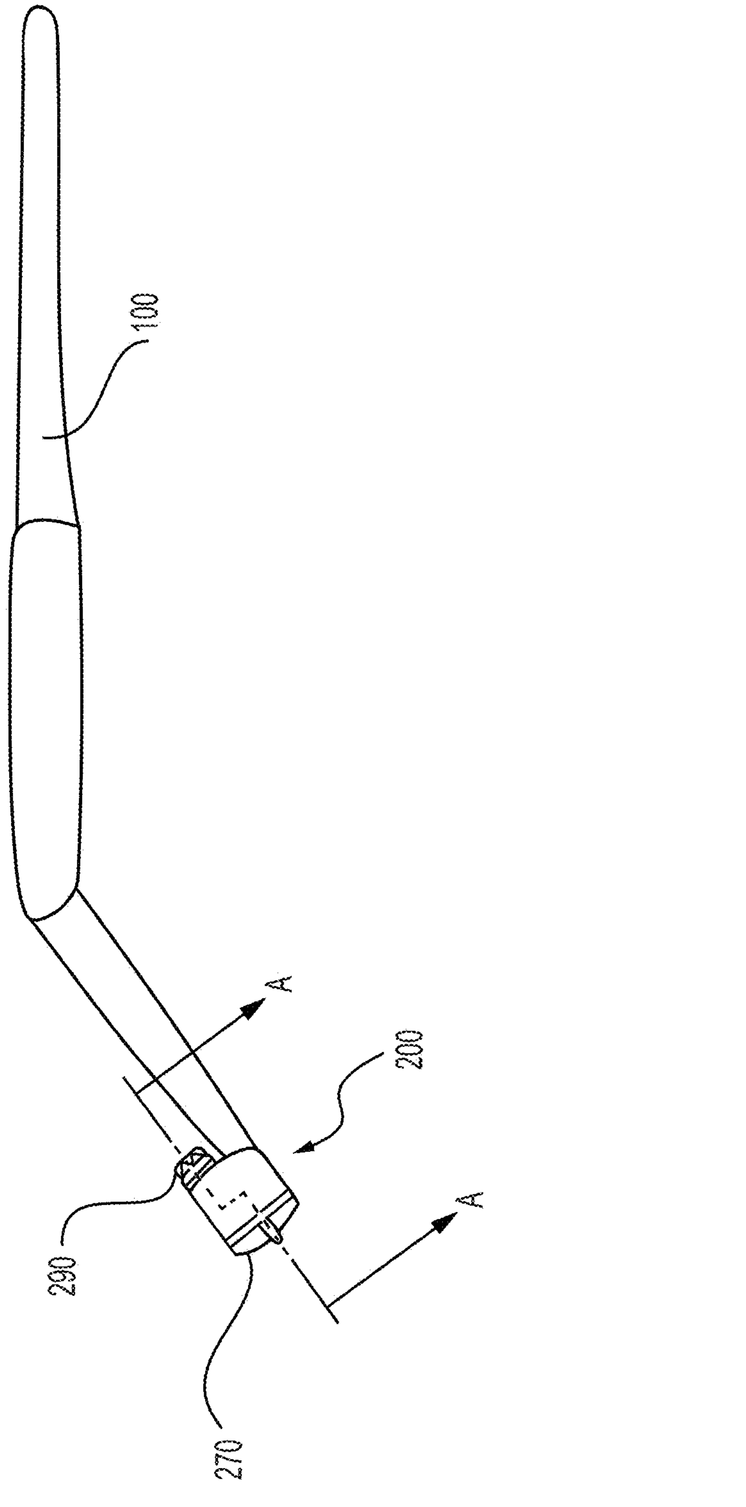
FIG. 2 is a side view illustrating a handle and a coupling mechanism of the surgical instrument of FIG. 1.

The handle 100 may have a bend along its length. For example, the handle may have a bend of about 135°, as illustrated in FIG. 2. Alternatively, the handle 100 may be straight. The coupling mechanism 200 includes a body 220, a first shank 250 movably connected to the body 220 and selectively affixable to the body 220, and a second shank 270 movably connected to the body 220 and selectively affixable to the body 220.

The body 220 of the coupling mechanism 200 may be connected to the handle 100. The first and second shanks 250, 270 may extend from opposite side surfaces of the body 220. The cutting tool 300 is selectively connectable to the first and second shanks 250, 270.

Figure 3:
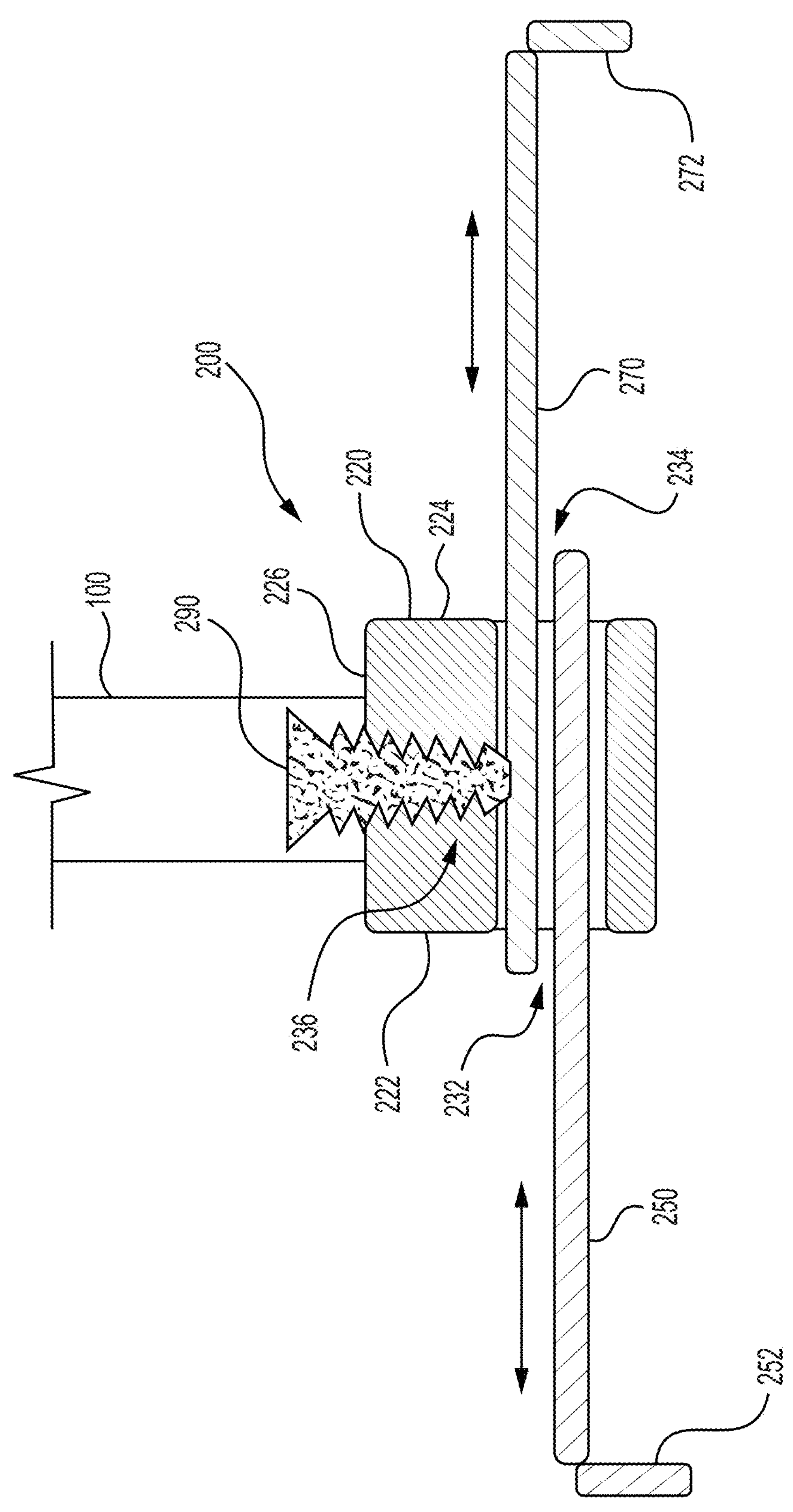
FIG. 3 is an exploded cross-sectional view taken along line A-A of FIG. 2.

Referring to FIG. 3, the body 220 may include a first side surface 222 and a first hole 232 extending into the body 220 from the first side surface 222. The body 220 may also include a second side surface 224 arranged opposite to the first side surface 222 and a second hole 234 extending into the body 220 from the second side surface 224.

The first shank 250 may extend at least partially in the first hole 232 and extend outwardly from the first side surface 222. The second shank 270 may extend at least partially in the second hole 234 and extend outwardly from the second side surface 224.

The first hole 232 and the second hole 234 may be in fluid communication with one another at a first interior portion of the body 220. For example, the first hole 232 and the second hole 234 may be in fluid communication with one another at an interior region of the body 220 where the first hole 232 and the second hole 234 overlap a fastener 290. As illustrated in FIG. 3, the first and second holes 232, 234 may form a through opening in the body 220 capable of accommodating the first and second shanks 250, 270 inside.

The body 220 may also include a third side surface 226, extending between the first and second side surfaces 222, 224 and a third hole 236, extending into the body 220 from the third side surface 226. The third hole 236 may be in fluid communication with the first and second holes 232, 234 at the first interior portion of the body 220. The fastener 290, which may be included in the coupling mechanism 200, is selectively connected to the body 220. The fastener 290 may extend in the third hole 236. The fastener 290 is configured to selectively affix the first and second shanks 250, 270 to the body 220 (and to one another) by pressing the first and second shanks 250, 270 against the body 220 at the first interior portion of the body 220.

As illustrated in FIG. 3, the fastener 290 may have a fastener body with threads along a length of the fastener body. The third hole 236 may have threads matching the threads of the fastener body along a length of the third hole 236. The fastener 290 and the third hole 236 may be threadedly connected to one another.

Figure 4:
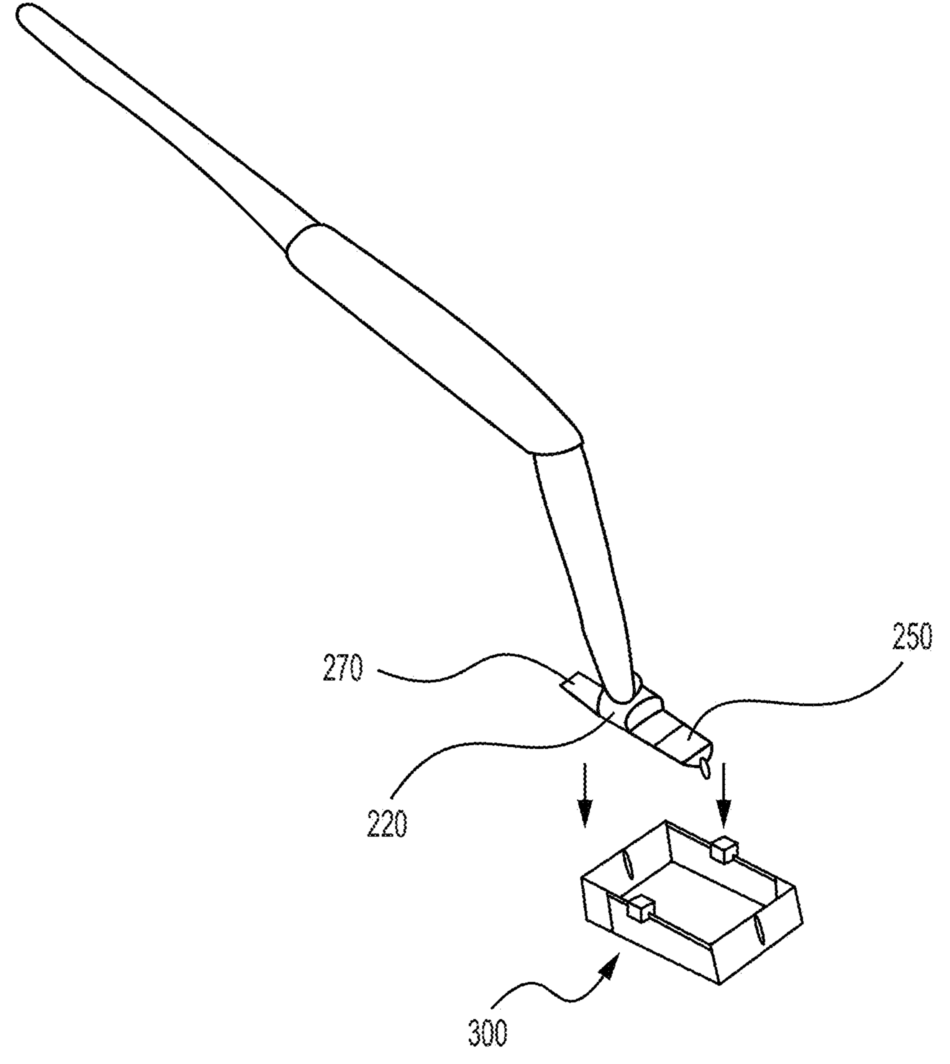
FIG. 4 is a perspective view illustrating connection of the handle and the coupling mechanism of the surgical instrument of FIG. 1 with a cutting tool.

The fastener 290 can be rotated in a first direction (e.g., clockwise) to clamp (e.g., selectively affix) the first and second shanks 250, 270 to the body 220 such that a length between distal ends of the first and second shanks 250, 270 matches a length of the cutting tool 300. Then, as illustrated in FIG. 4, the handle 100 with the first and second shanks 250, 270 can be selectively connected to the cutting tool 300 to produce a surgical instrument as illustrated in FIG. 1.

The fastener 290 can be rotated in a second direction (e.g., counterclockwise) to release the clamping action on the first and second shanks 250, 270 such that the first and second shanks 250, 270 can be moved relative to the body 220 for various purposes. For example, by loosening the fastener 290 to free the first and second shanks 250, 270 to move relative to the body 220, the first and second shanks 250, 270 can be retracted, enabling a worn out cutting tool 300 to be removed and replaced with a new, sharp cutting tool 300, to be retracted or expanded, enabling a cutting tool of a different length to be selectively coupled to the first and second shanks 250, 270, etc., as the case may be.

The cutting tool 300 may have an elongated hollow polygonal shape (e.g., an elongated hollow polygonal section). In a non-liming example, the cutting tool 300 may have an elongated hollow rectangular shape.

Figure 6:
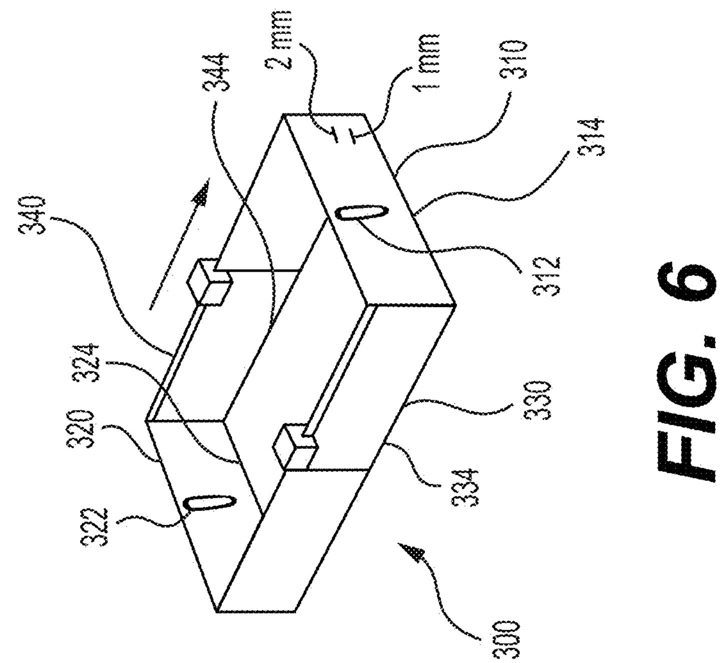
FIG. 6 is a perspective view illustrating the cutting tool of the surgical instrument of FIG. 1 in an extended state.
Figure 5:
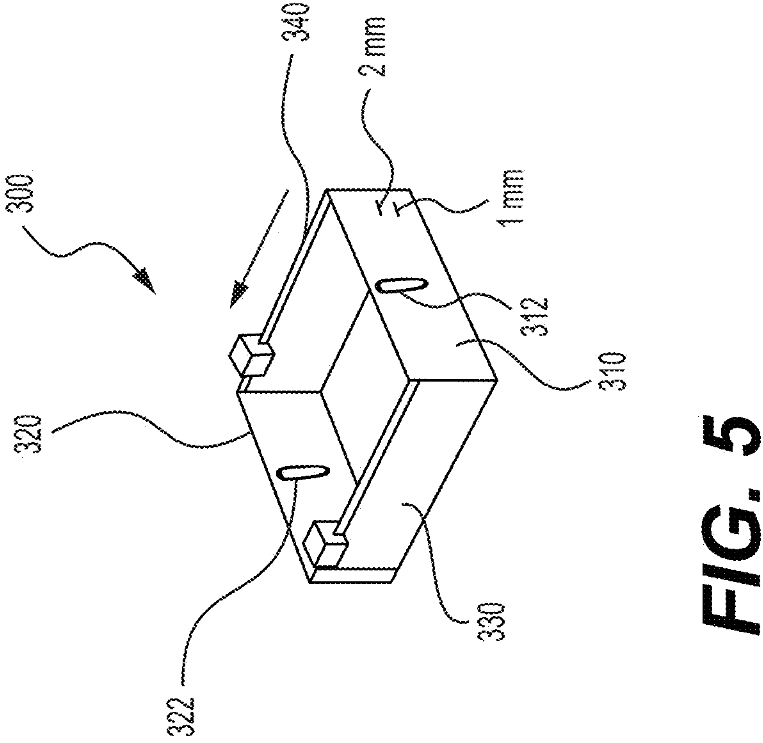
FIG. 5 is a perspective view illustrating the cutting tool of the surgical instrument of FIG. 1 in a retracted state.

Referring to FIGS. 5 and 6, the cutting tool 300 may include first and second blades 310, 320 spaced apart from one another and opposing one another, and third and fourth blades 330, 340 spaced apart from one another and opposing one another. A "blade," as described herein, may alternatively be referred to as a "sidewall" of the elongated hollow polygonal cutting tool 300, since each sidewall of the cutting tool 300 may define a cutting blade.

The third blade 330 may connect the first and second blades 310, 320 to one another, and the fourth blade 340 may connect the first and second blades 310, 320 to one another. Referring to FIGS. 5 and 3, the first blade 310 may have a first blade hole 312 and the first shank 250 may have a first protrusion 252 configured to be selectively inserted in the first blade hole 312 to selectively connect the first shank 250 with the first blade 310.

The second blade 320 may have a second blade hole 322 and the second shank 270 may have a second protrusion 272 configured to be selectively inserted in the second blade hole 322 to selectively connect the second shank 270 with the second blade 320.

Each blade of the cutting tool 300 may have a cutting edge (e.g., a sharp edge), formed on an end of the cutting tool 300 that is distal from (or opposite to) the handle 100. For example, with reference to FIG. 6, the first blade 310 may have a first cutting edge 314, the second blade 320 may have a second cutting edge 324, the third blade 330 may have a third cutting edge 334 and the fourth blade 340 may have a fourth cutting edge 344.

The first cutting edge 314, the second cutting edge 324, the third cutting edge 334 and the fourth cutting edge 344 may extend along the same plane. The co-planar arrangement between the first to fourth cutting edges 314 to 344 can be used to make a cut having a substantially even (or equal) depth all around the perimeter of the cut—in a soft tissue site of a patient—by using the instrument of FIG. 1.

One or more of the first to fourth blades 310 to 340 may have one or more markings on its exterior for indicating a depth of insertion of the first to fourth cutting edges 314 to 344. See FIGS. 5 and 6, illustrating a 1 mm depth marking and a 2 mm depth mark markings on the exterior of the third blade 330, merely as an example. The number of depth markings may be varied as needed.

The cutting tool 300 may have an adjustable length. For example, in the non-limiting embodiment of FIGS. 1-8, the third blade 330 may have an adjustable length and the fourth blade 340 may have an adjustable length. In this non-limiting embodiment, the first blade 310 and the second blade 320 have a fixed length.

Figures 7, 8, 9:
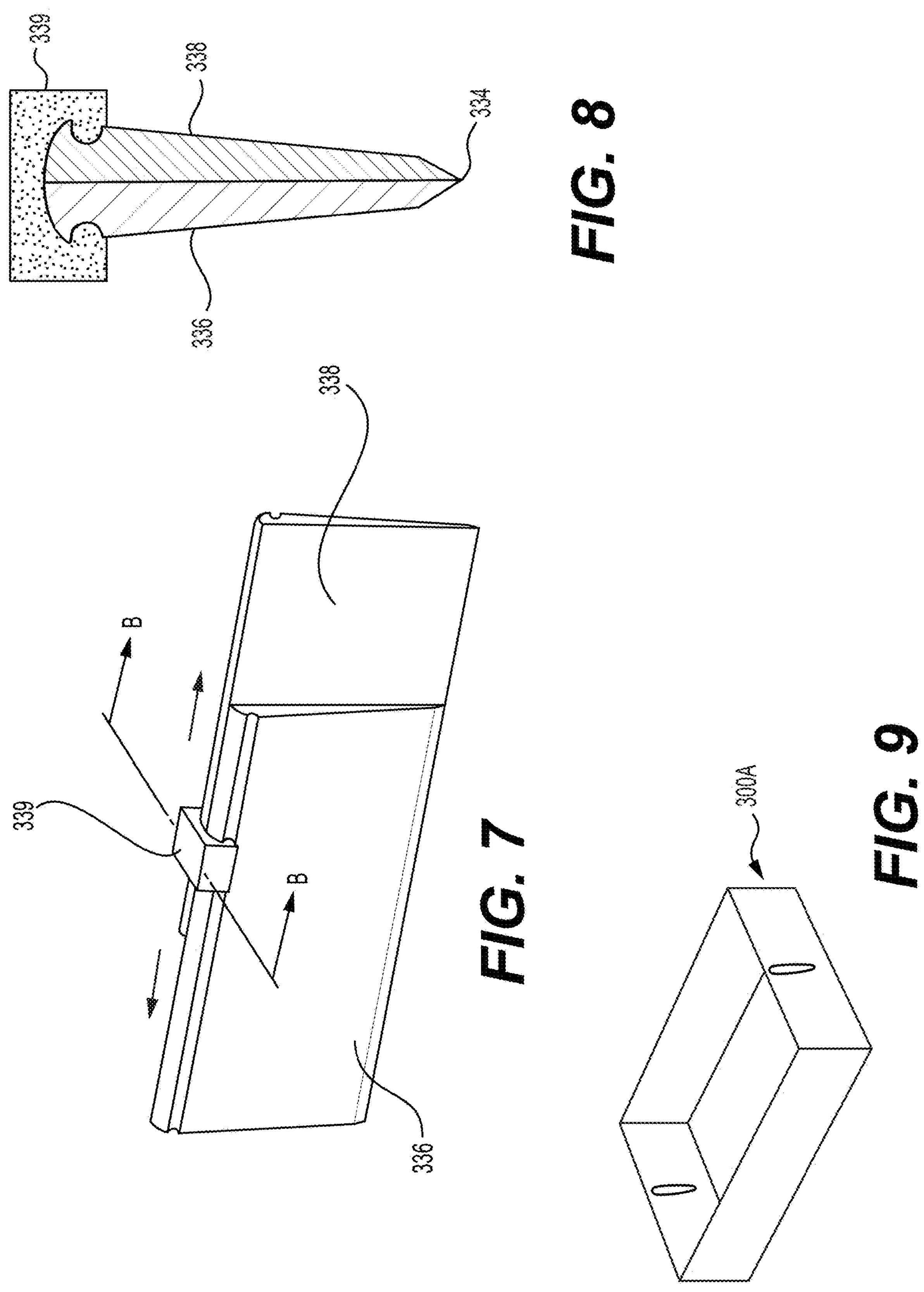
FIG. 7 is a perspective view illustrating a length-adjustable sidewall of the cutting tool of FIGS. 5 and 6.
FIG. 8 is a cross-sectional view taken along line B-B of FIG. 7.
FIG. 9 is a perspective view illustrating a fixed length cutting tool according to an embodiment of the present subject matter.

As illustrated in FIGS. 7 and 8, the third blade 330 may include a first blade portion 336 extending between the first and second blades 310, 320, and a second blade portion 338 extending between the first and second blades 310, 320 and overlapping the first blade portion 336. The first blade portion 336 may be fixedly connected to the first blade 310 and movably connected to the second blade portion 338. The second blade portion 338 may be fixedly connected to the second blade 320 and movably connected to the first blade portion 336.

As illustrated in FIGS. 5-8, the cutting tool 300 may include a first clip 339 slidably connecting the first and second blade portions 336, 338 of the third blade 330 to one another. The fourth blade 340 may be configured substantially similarly to the third blade 330. As such, a detailed description of the fourth blade 340 may be omitted for brevity.

Alternatively, or in addition, a cutting tool that can be selectively connected to a coupling mechanism 200 of the present subject matter can have a fixed length. FIG. 9 shows an exemplary cutting tool 300A of fixed dimensions. The cutting tool 300A of FIG. 9 may be generally similar to the cutting tool 300 of FIG. 1, except for having first to fourth blades of a fixed length. In addition, the dimensions of the cutting tool 300A may be similar to or different from the dimensions of the cutting tool 300.

Based on the teachings herein, cutting tools of different dimensions, whether fixed or adjustable, can be used with a hand apparatus formed by the handle 100 and the coupling mechanism 200 due to the ability of the first and second shanks to be retracted or extended relative to the body 220 of the coupling mechanism 200.

A method of performing a surgical procedure includes obtaining the surgical instrument as described herein with reference to FIGS. 1-8. The method may include selectively connecting a cutting tool, as described above, to the first and second shanks 250, 270 (when the handle 100 and the coupling mechanism 200 are assembled or connected to one another as illustrated in FIG. 2). When the cutting tool is selectively connected to the first and second shanks 250, 270, the method includes directing the cutting tool toward a surgical site of a patient's body (e.g., toward a soft tissue donor site). The method further includes pressing the cutting tool toward the patient's body, causing the cutting tool to cut into soft tissue at the soft tissue donor site. See FIG. 11, illustrating the step of pressing the cutting tool 300 toward a patient's body. For example, a user (e.g., a surgeon or other medical professional), can grasp the handle 100 and manipulate the handle 100 to cause the cutting tool 300 to be pressed against the soft tissue donor site. FIG. 12 shows a perimeter 400 of the cut caused by pressing the cutting tool 300 into the patient's soft tissue and a donor tissue graft 410 being delineated by the perimeter 400 of the cut. The donor tissue graft 410 may have a substantially even depth across its surface due to the shape of the cutting tool 300.

The soft tissue graft 410 of FIG. 12 can be removed using various apparatuses and methods of extraction, and can be grafted, as shown in the example of FIG. 13, under the incisors of the lower jaw to cover exposed roots 420 of the incisors, as illustrated in FIG. 10. The cutting tool 300 can be sized and shaped to cut a soft tissue graft having a desired shape, size and depth. In an approach, the cutting tool used can have a fixed size that is suitable for a medical procedure that a patient will be subjected to. In another approach, an adjustable cutting tool, for example, the cutting tool 300 described in this specification, can be employed and adjusted according to the size and shape of the graft that needs to be obtained.

When using an adjustable cutting tool, the method may include adjusting the separation distance between the first and second sidewalls as taught by this specification by pulling the first and second sidewalls toward one another or by pushing the first and second sidewalls away from one another, thereby causing the first and second blade portions to move relative to one another and causing the third and fourth blade portions to move relative to one another.

The method may include adjusting a distance by which the first and second shanks 250, 270 extend from the opposite side surfaces 222, 224 of the body 220 based on a separation distance between the first and second sidewalls of the cutting tool used prior to the step of connecting the cutting tool to the first and second shanks 250, 270.

The step of connecting the cutting tool to the first and second shanks 250, 270 may include inserting the first protrusion 252 of the first shank 250 in the first blade hole 312 and inserting the second protrusion 272 of the second shank 270 in the second blade hole 322.

The method may also include loosening the fastener 290, thereby enabling the first and second shanks 250, 270 to be moved relative to the body 220, prior to carrying out the step of adjusting the distance, by which the first and second shanks 250, 270 extend from the opposite side surfaces of the body 220; and, after having carried out the step of adjusting the distance by which the first and second shanks 250, 270 extend from said opposite side surfaces of the body 220, tightening the fastener 290 to affix the first and second shanks 250, 270 to the body 220 of the coupling mechanism 200.

It is to be understood that the surgical instrument and the method of using the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

What is claimed is:

1. A surgical instrument, comprising:

a handle;

a coupling mechanism connected to the handle, wherein the coupling mechanism comprises:

a body;

a first shank movably connected to the body and selectively affixable to the body; and a second shank movably connected to the body and selectively affixable to the body, wherein the first and second shanks extend from opposite side surfaces of the body; and a cutting tool selectively connectable to the first and second shanks.

2. The surgical instrument of claim 1, wherein the body comprises:

a first side surface and a first hole extending into the body from said first side surface; and a second side surface arranged opposite to the first side surface and a second hole extending into the body from said second side surface, wherein the first shank extends at least partially in the first hole and extends outwardly from the first side surface, and the second shank extends at least partially in the second hole and extends outwardly from the second side surface.

3. The surgical instrument of claim 2, wherein the first hole and the second hole are in fluid communication with one another at a first interior portion of the body, and wherein the body further comprises:

a third side surface, extending between the first and second side surfaces thereof; and a third hole, extending into the body from the third side surface thereof, wherein the third hole is in fluid communication with the first and second holes at the first interior portion of the body.

4. The surgical instrument of claim 3, wherein the coupling mechanism further comprises a fastener selectively connected to the body, wherein the fastener extends through the third hole and is configured to selectively affix the first and second shanks to the body by pressing the first and second shanks against the body at the first interior portion of the body.

5. The surgical instrument of claim 4, wherein the fastener has a fastener body with threads along a length thereof, and the third hole has threads matching the threads of the fastener body along a length of the third hole, wherein the fastener and the third hole are threadedly connected to one another.

6. The surgical instrument of claim 1, wherein the cutting tool comprises:

first and second blades spaced apart from one another and opposing one another; and third and fourth blades spaced apart from one another and opposing one another, wherein the third blade connects the first and second blades to one another, and the fourth blade connects the first and second blades to one another.

7. The surgical instrument of claim 6, wherein the first blade has a first blade hole and the first shank has a first protrusion configured to be selectively inserted in the first blade hole to selectively connect the first shank with the first blade.

8. The surgical instrument of claim 7, wherein the second blade has a second blade hole and the second shank has a second protrusion configured to be selectively inserted in the second blade hole to selectively connect the second shank with the second blade.

9. The surgical instrument of claim 6, wherein the first blade has a first cutting edge, the second blade has a second cutting edge, the third blade has a third cutting edge and the fourth blade has a fourth cutting edge.

10. The surgical instrument of claim 9, wherein the first cutting edge, the second cutting edge, the third cutting edge and the fourth cutting edge extend along a same plane.

11. The surgical instrument of claim 9, wherein at least one of the first blade, the second blade, the third blade and the fourth blade has one or more markings thereon for indicating a depth of insertion of the first cutting edge.

12. The surgical instrument of claim 8, wherein the third blade has a fixed length and the fourth blade has a fixed length.

13. The surgical instrument of claim 8, wherein the third blade has an adjustable length and the fourth blade has an adjustable length.

14. The surgical instrument of claim 13, wherein the third blade comprises:

a first blade portion extending between the first and second blades; and a second blade portion extending between the first and second blades and overlapping the first blade portion, wherein the first blade portion is fixedly connected to the first blade and movably connected to the second blade portion, and wherein the second blade portion is fixedly connected to the second blade.

15. The surgical instrument of claim 14, wherein the cutting tool further includes a first clip slidably connecting the first and second blade portions of the third blade to one another.

16. A method of performing a surgical procedure, comprising:

providing the surgical instrument according to claim 1;

connecting the cutting tool to the first and second shanks;

directing the cutting tool toward a surgical site of a patient's body; and pressing the cutting tool toward the patient's body, causing the cutting tool to cut into soft tissue at the surgical site.

17. The method of claim 16, wherein the cutting tool is a polygonal hollow section having a plurality of sidewalls with sharp edges opposite to the handle, wherein a first sidewall of the plurality of sidewalls includes a first blade hole and the first shank has a first protrusion configured to be selectively inserted in the first blade hole to selectively connect the first shank with the first sidewall, wherein a second sidewall of the plurality of sidewalls includes a second blade hole and the second shank has a second protrusion configured to be selectively inserted in the second blade hole to selectively connect the first shank with the second sidewall, wherein the first and second sidewalls are opposite to one another and separated from one another, wherein a third sidewall of the plurality of sidewalls and a fourth sidewall of the plurality of sidewalls are opposite to one another and separated from one another, and wherein the third sidewall and the fourth sidewall, respectively, connect the first sidewall and the second sidewall to one another, the method further comprising adjusting a distance by which the first and second shanks extend from said opposite side surfaces of the body based on a separation distance between the first and second sidewalls prior to the step of connecting the cutting tool to the first and second shanks, wherein the connecting of the cutting tool to the first and second shanks includes inserting the first protrusion of the first shank in the first blade hole and inserting the second protrusion of the second shank in the second blade hole.

18. The method of claim 17, further comprising:

loosening a fastener connected to the body of the coupling mechanism, thereby enabling the first and second shanks to be moved relative to the body, prior to carrying out the step of adjusting the distance by which the first and second shanks extend from said opposite side surfaces of the body; and after having carried out the step of adjusting the distance by which the first and second shanks extend from said opposite side surfaces of the body, tightening the fastener to affix the first and second shanks to the body of the coupling mechanism.

19. The method of claim 16, wherein the cutting tool has an adjustable length, wherein the third sidewall includes a first blade portion extending between the first and second sidewalls and a second blade portion extending between the first and second sidewalls, said second blade portion overlapping the first blade portion, wherein the first blade portion is fixedly connected to the first sidewall and movably connected to the second blade portion, and wherein the second blade portion is fixedly connected to the second sidewall;

wherein the fourth sidewall includes a third blade portion extending between the first and second sidewalls and a fourth blade portion extending between the first and second sidewalls and overlapping the third blade portion, wherein the third blade portion is fixedly connected to the first sidewall and movably connected to the second blade portion, and wherein the fourth blade portion is fixedly connected to the second sidewall;

the method further comprising adjusting the separation distance between the first and second sidewalls by pulling the first and second sidewalls toward one another or by pushing the first and second sidewalls away from one another, thereby causing the first and second blade portions to move relative to one another and causing the third and fourth blade portions to move relative to one another.

20. A surgical instrument, comprising:

a handle;

a coupling mechanism connected to the handle, wherein the coupling mechanism comprises:

a body;

a first shank movably connected to the body and selectively affixable to the body; and a second shank movably connected to the body and selectively affixable to the body, wherein the first and second shanks extend from opposite side surfaces of the body; and a cutting tool selectively connectable to the first and second shanks, wherein the cutting tool is an elongated polygonal hollow section having a plurality of sidewalls with sharp edges opposite to the handle, wherein a first sidewall of the plurality of sidewalls includes a first blade hole and the first shank has a first protrusion configured to be selectively inserted in the first blade hole to selectively connect the first shank with the first sidewall, wherein a second sidewall of the plurality of sidewalls includes a second blade hole and the second shank has a second protrusion configured to be selectively inserted in the second blade hole to selectively connect the first shank with the second sidewall, wherein the first and second sidewalls are opposite to one another and separated from one another, wherein a third sidewall of the plurality of sidewalls and a fourth sidewall of the plurality of sidewalls are opposite to one another and separated from one another, wherein the third sidewall and the fourth sidewall, respectively, connect the first sidewall and the second sidewall to one another, and wherein, when the first and second shanks are selectively connected to one another, the first and second shanks extend in a cavity of the polygonal hollow section, between said first to fourth sidewalls.

* * * * *